(12) United States Patent
Leung

(10) Patent No.: US 9,365,475 B2
(45) Date of Patent: Jun. 14, 2016

(54) ALKOXYLATION OF CRUDE BISPHENOL A

(71) Applicant: BAKER HUGHES INCORPORATED, Houston, TX (US)

(72) Inventor: Philip L. Leung, Houston, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 151 days.

(21) Appl. No.: 14/164,433

(22) Filed: Jan. 27, 2014

(65) Prior Publication Data

US 2014/0142345 A1 May 22, 2014

Related U.S. Application Data

(63) Continuation-in-part of application No. 12/645,812, filed on Dec. 23, 2009, now abandoned, which is a continuation-in-part of application No. 11/443,630, filed on May 31, 2006, now abandoned.

(51) Int. Cl.
*C07C 41/03* (2006.01)
*C07C 41/09* (2006.01)
*C08G 65/26* (2006.01)
*C08G 65/30* (2006.01)

(52) U.S. Cl.
CPC .............. *C07C 41/09* (2013.01); *C07C 41/03* (2013.01); *C08G 65/2609* (2013.01); *C08G 65/2648* (2013.01); *C08G 65/30* (2013.01)

(58) Field of Classification Search
None
See application file for complete search history.

(56) References Cited

U.S. PATENT DOCUMENTS

| 2,135,128 | A | | 11/1938 | Thomas et al. | |
|---|---|---|---|---|---|
| 2,938,884 | A | | 5/1960 | Chern | |
| 3,374,286 | A | | 3/1968 | Hicks | |
| 3,719,636 | A | | 3/1973 | Wojtowicz et al. | |
| 4,241,201 | A | * | 12/1980 | Annis | 525/503 |
| 4,469,820 | A | * | 9/1984 | Dexheimer et al. | 521/125 |
| 4,846,996 | A | | 7/1989 | Carroll et al. | |
| 4,906,789 | A | * | 3/1990 | Grzywa et al. | 568/727 |
| 5,227,436 | A | | 7/1993 | Cavitt et al. | |
| 5,362,822 | A | | 11/1994 | Hefner, Jr. | |
| 5,463,133 | A | | 10/1995 | Sato et al. | |
| 6,444,858 | B2 | | 9/2002 | Leung | |
| 6,541,673 | B1 | * | 4/2003 | Rodriguez et al. | 568/633 |
| 6,624,333 | B1 | | 9/2003 | Koser et al. | |
| 2005/0240064 | A1 | | 10/2005 | Weerasooriya et al. | |
| 2006/0004232 | A1 | | 1/2006 | Wulff et al. | |
| 2006/0052648 | A1 | | 3/2006 | Wulff et al. | |

* cited by examiner

*Primary Examiner* — Rosalynd Keys
(74) *Attorney, Agent, or Firm* — Mossman Kumar & Tyler PC

(57) ABSTRACT

Crude bisphenol A containing a ketone solvent remaining form its manufacture and having a melting point of 150° C. or higher may be reacted with one or more alkylene oxide, in the absence of any added ketone solvent, at reduced temperatures compared with conventional, molten methods to give a fully alkoxylated adduct product having reduced color. By at least partially alkoxylating the bisphenol A, its potential for crystallization is disrupted and the partially alkoxylated bisphenol A has a lower melting point than the original bisphenol A permitting it to be more readily further alkoxylated at the reaction temperature. The alkoxylation reaction may be conducted at a temperature in the range of about 30 to about 140° C. Suitable catalysts may include tertiary amines or caustic compounds such as NaOH and KOH.

19 Claims, No Drawings

ALKOXYLATION OF CRUDE BISPHENOL A

CROSS-REFERENCE TO RELATED APPLICATION

This application is a continuation-in-part application of U.S. Ser. No. 12/645,812 filed Dec. 23, 2009, which is a continuation-in-part application of U.S. Ser. No. 11/443,630 filed May 31, 2006, now abandoned, both of which are incorporated in their entirety herein by reference.

TECHNICAL FIELD

The present invention relates to methods for alkoxylating high melting point substrates having active hydrogens, and more particularly relates, in one embodiment, to methods for alkoxylating substrates having active hydrogens, such as bisphenol A, without having to heat the substrates to the high temperatures required to melt them, thus reducing undesirable by-products and colors. The present invention also relates to methods for alkoxylating high melting point substrates, which otherwise require special reactor systems heated by hot oil, instead permitting more commonly available reactor system heated by steam to be used, thus eliminating the need and expense to specially insulate and heat-trace the pipes and valves and further avoid problems with plugging of pipes and valves by solidified materials.

BACKGROUND

It has long been known to react substrates having active hydrogen atoms with alkylene oxides to give products useful in specialty plastics and as surfactants. For instance, bisphenol A (4,4'-isopropylidenediphenol or 2,2-bis(4-hydroxyphenol)propane), is known as an intermediate for epoxy resins and poly-carbonate resins. The reaction of bisphenol A with ethylene oxide (EO) may be typically done without a solvent in a molten state at temperatures in the range of about 160 to about 170° C. However, it is well recognized that ethylene oxide is very volatile, and at these temperatures there are safety concerns. Disadvantages of producing EO adducts of bisphenol A at these temperatures include the requirement of using a special, oil-heated reactor system that is more costly as compared with a more commonly used steam-heated reactor system that most operators prefer. Conventionally, alkoxylating high melting point substrates, such as bisphenol A, requires special insulation of and heat-tracing of the pipes, valves and other equipment. Also, the substrates can readily solidify during the taking of samples for analysis, which solidification causes plugging of valves and lines and which, in turn, creates costly down-time and shut-time of the reactor and/or manufacturing process. Further, heating such substrates to their melting points for alkoxylation increases the tendency of the formation of more undesirable degradation products, by-products and color, possibly due to the effects of heating the product. There has been considerable effort over at least the last ten years by many companies to alkoxylate high melting point substrates but avoiding a discolored product, without success.

It would thus be desirable to provide a method for alkoxylating substrates with active hydrogens that could be conducted at relatively lower temperatures to reduce safety concerns, to allow the use of more commonly available and less costly steam-heated reactor systems, and also to possibly reduce the color of and the amount of undesirable degradation by-products in the alkoxylated product.

SUMMARY

There is provided, in one non-restrictive embodiment, a method for producing a fully alkoxylated bisphenol A that involves mixing a compound that is an alkylene oxide and/or an arylene oxide, with crude bisphenol A containing a ketone solvent remaining from the manufacture of the crude bisphenol A, with a catalyst to give a reaction mixture, where the catalyst is a tertiary amine catalyst and/or a caustic compound including, but not necessarily limited to potassium hydroxide and/or sodium hydroxide, where the method further involves reacting the compound with the bisphenol A in the reaction mixture at a reaction temperature in the range of about 30 to 140° C. to give an at least partially alkoxylated bisphenol A that is sufficiently alkoxylated to lower its melting point below the reaction temperature, and continuing to alkoxylate the at least partially alkoxylated bisphenol A, where the method is conducted in the absence of added ketone solvent, to give a fully alkoxylated product. It should be understood that "in the absence of additional added ketone solvent" means in the absence of any added ketone solvent, whether or not the ketone solvent is the same as that contained in the crude bisphenol A.

In another non-limiting embodiment, there is provided a method that concerns producing a fully alkoxylated bisphenol A, where the method involves mixing crude bisphenol A containing a ketone solvent remaining from the manufacture of the crude bisphenol A, with a caustic compound catalyst to give a mixture, where the catalyst may be potassium hydroxide and/or sodium hydroxide; heating the mixture to dehydrate it; adding a compound including, but not necessarily limited to alkylene oxide and/or arylene oxide, to the mixture to give a reaction mixture; reacting the compound with the bisphenol A in the reaction mixture at a reaction temperature in the range of about 30 to 140° C. to give an at least partially alkoxylated bisphenol A sufficiently alkoxylated to lower its melting point below the reaction temperature; and continuing to alkoxylate the at least partially alkoxylated bisphenol A to give the fully alkoxylated bisphenol A. The method is conducted in the absence of added ketone solvent.

There is additionally provided in another non-restrictive embodiment a method for producing a fully alkoxylated bisphenol A that includes mixing crude bisphenol A containing a ketone solvent remaining from the manufacture of the crude bisphenol A, with a tertiary amine catalyst to give a mixture; adding a compound including, but not necessarily limited to, alkylene oxide and/or arylene oxide, to the mixture to give a reaction mixture; reacting the compound with the bisphenol A in the reaction mixture at a temperature in the range of about 30 to 140° C. to give an at least partially alkoxylated bisphenol A sufficiently alkoxylated to lower its melting point below the reaction temperature; and continuing to alkoxylate the at least partially alkoxylated bisphenol A to give the fully alkoxylated bisphenol A; where the method is conducted in the absence of added ketone solvent.

DETAILED DESCRIPTION

It has been discovered that substrates or starter molecules having active hydrogen atoms (in a non-limiting example, bisphenol A) and other high melting point substrates as well, may be reacted with multiple equivalents of an alkylene oxide (in another non-restrictive instance, ethylene oxide), arylene oxide and/or epoxy or oxirane compound in the presence of a catalyst and a ketone solvent at a reduced temperature compared to the conventional molten process, to give an adduct or product having reduced color and by-products or impurities.

This method also provides an alternative method of conducting ethoxylations of bisphenol A and other relatively high melting point substrates soluble in ketone or other solvent with a bigger choice in the type and design of reactor system that may be used when these products produced by conventional methods are in short supply.

It has been further discovered that crude bisphenol A which contains a ketone solvent (e.g. acetone) remaining from its manufacture may be mixed with an alkylene oxide and/or an arylene oxide and reacted therewith in the presence of a catalyst at reaction temperature to give an at least partially alkoxylated bisphenol A, which has been sufficiently alkoxylated to lower its melting point below the reaction temperature—thereby keeping it in solution—and continuing to alkoxylated the bisphenol A to give a fully alkoxylated bisphenol A, all without (or in the absence of) any added ketone solvent. Typically, the manufacture of the crude bisphenol A will involve adding a ketone. However, it has been discovered that the ketone solvent that remains in the crude bisphenol A is sufficient to permit the method discovered herein to proceed without having to add more or additional ketone solvent. This embodiment has the advantages of using a less expensive substrate (crude bisphenol A as compared with pure or substantially pure BPA) and requiring no additional or added ketone solvent, or the equipment and procedures involved in handling and introducing additional ketone solvent. Again, it should be understood that "in the absence of additional added ketone solvent" means in the absence of any added or additional ketone solvent, whether or not the ketone solvent is the same as that contained in the crude bisphenol A.

In one non-limiting embodiment the method has an absence of, or is conducted without, substantially pure bisphenol A. In another non-restrictive embodiment, by "substantially pure" is meant at least 99 wt % pure.

By "high melting point" is meant having a melting point of 150° C. or higher. For example, bisphenol A has a melting point of about 158-159° C.

A goal of the method is to incorporate onto the substrate at least a minimal amount of oxide to disrupt the crystallinity of the molecular structures and thereby disrupt the solidification process such that the substrate would no longer solidify at the highest normal alkoxylation temperatures, in one non-limiting embodiment, about 140° C. This permits the at least partially alkoxylated substrate (e.g. bisphenol A) to remain molten and facilitate its continued alkoxylation until the method gives a fully alkoxylated product. "Fully alkoxylated" is defined herein to mean the point at which all of the desired and/or intended alkylene oxide and/or arylene oxide is added to the substrate (e.g. bisphenol A). This point may also be understood to be complete alkoxylation. This definition is irrespective of whether further alkoxylation is chemically possible.

The method described herein takes advantage of the facts that 1) one of the raw materials for making of bisphenol A is also a solvent for bisphenol A (i.e. a ketone), 2) this raw material is not reactive towards an alkylene oxide or an arylene oxide, 3) the fact that crude bisphenol A is significantly less expensive as a feedstock since no purification steps are needed prior to the method described herein, 4) the crude bisphenol A is a fluid solution, which makes it easier to package, transport, handle and use compared to solid bisphenol A that has a high melting point, and 5) partially alkoxylated bisphenol A will have a lower melting-point to allow continuation of alkoxylation at lower reaction temperatures.

The temperatures at which the methods herein may be practiced may range from about 30 independently to about 160° C., in another non-restrictive embodiment from a lower threshold of about 80 independently to an upper threshold of about 130° C. (alternatively 140° C.), as contrasted with the higher range from a lower threshold of about 160 independently to an upper threshold of about 170° C. for a conventional molten process. Alternatively, the methods herein may be practiced at a temperature from about 30 independently to about 140° C. or even up to about 150° C. As used herein with respect to a range, the term "independently" means that other ranges may be suitable made by combining any of the lower thresholds with any of the higher thresholds. Without wishing to be limited to any particular theory or explanation, it is believed that exposure of the alkoxylated products to the relatively higher temperature produces more undesirable by-products and degradation impurities, and more color bodies thereby coloring the product.

The starter molecule or substrate may be any of a wide variety of compounds as long as they possess one or more active hydrogens to react with the alkylene oxide. Solubility in ketone is helpful in one non-limiting embodiment. Suitable substrates include, but are not necessarily limited to, diols and polyols (e.g. glycerin, trimethylolpropane, pentaerythritol, sucrose, sorbitol, and the like, and ethylene glycol, propylene glycol, neopentyl glycol and other glycols such as 2,3,4-trimethyl-1,3-pentanediol (m.p. 46-55° C.)), various phenols (such as various mono-, di- or tri-alkyl phenols and the like), polyphenols, (e.g. bisphenol A (BPA)), primary amines, secondary amines as well as polyfunctional amines (such as ethylenediamine, toluenediamine, diethylene triamine, tetraethylene triamine and the like), compounds with both amino and hydroxyl group(s) (such as ethanol amines, tris(hydroxymethyl)aminomethane (TRIS, $H_2NC(CH_2OH)_3$ and the like), various carboxylic acids (such as oleic acid, stearic acids, tall oil fatty acids, and the like), compounds with both amino and carboxylic group(s) such as various amino-acids, and mixtures thereof. The substrate may optionally be a prepolymer, for a non-restrictive instance in the process to make a polyol. The reaction to make the prepolymer may be run in the absence of a ketone or other solvent, and then the prepolymer may be further alkoxylated in the presence of a ketone or other solvent to make the finished product, e.g. a polyol. For the purposes of illustration only, bisphenol A will typically be used as an illustrative example of a suitable substrate herein, but it will be understood that other reactants such as those listed and those not listed but which would still function for the purposes of the methods herein are included. In another non-limiting embodiment the substrate is crude bisphenol A containing a ketone solvent remaining from the manufacture of the crude bisphenol A.

Similarly, a wide variety of alkylene oxides, arylene oxide and/or epoxy or oxirane compounds may be used in the methods here, including, but not necessarily limited to, ethylene oxide (EO), propylene oxide (PO), butylenes oxide, styrene oxide, other epoxides or epoxy compounds and mixtures thereof. It is expected that in most cases the alkylene oxide will be EO and/or PO. In the case where more than one alkylene oxide is used, the alkylene oxides may be added sequentially as blocks or randomly as a mixture. There is no particular limit to the amount of alkylene oxide that may be added. For purposes of illustration only, ethylene oxide will typically be used herein as an illustrative, but not limiting example of a suitable alkylene oxide, arylene oxide, epoxy or oxirane compound. It will be appreciated that in the context and method herein the term "alkoxylated product" includes products that have been reacted with arylene oxides (e.g. styrene oxide), epoxy compounds, as well as mixed arylene oxides and alkylene oxides.

In the methods herein there are two primary types of catalysts that may be used, caustic compounds or tertiary amines, although others may be known or discovered, and in its broadest sense, the methods described herein is not limited to a particular catalyst type. In one non-limiting embodiment the proportion of catalyst to the starting mixture of substrate and solvent may be about 1 wt %. The total amount of catalyst used may range from about 0.05 independently to about 5 wt % or higher, alternatively from about 0.1 independently to about 0.5 wt % (which is somewhat dependent on the particular catalyst and the particular alkylene oxide and/or arylene oxide used and on the relative amount of alkylene oxide and/or arylene oxide that will be reacted) of the finished adduct or product material. Generally one or more catalyst may be used. In one non-limiting embodiment only one, single catalyst is used.

In the case where a caustic compound is used as the catalyst, suitable catalysts include, but are not necessarily limited to, potassium hydroxide, sodium hydroxide, and mixtures thereof. In one non-limiting embodiment, when the caustic catalyst is added to the mixture of substrate and ketone, water evolves and should be removed in a dehydration step. Further, once the alkylene oxide is reacted, and prior to removal of the solvent and recovery of the product, the caustic catalyst is preferably neutralized. Suitable neutralizing agents include, but are not necessarily limited to, organic or mineral acidic compounds such as acetic acid, glycolic acid, phosphoric acid, hypophosphorous acid and the like and mixtures thereof.

In the case where the catalyst is a tertiary amine, suitable amines include, but are not necessarily limited to, triethylamine, tributyl amine, dimethylethylamine, methyldiethylamine, other methyl or dimethyl alkyl amines, and the like and mixtures thereof. When a tertiary amine is used as a catalyst, it is expected that the dehydration procedure and/or neutralization procedure need not be employed. These features may provide some advantages of using tertiary amines as catalysts instead of a caustic compound.

In an alternate non-limiting embodiment, the method is practiced in the absence of a phosphine catalyst or the absence of a substituted phosphine catalyst.

As noted, an important feature of one embodiment of the method herein is the optional use of additional ketone solvent which permits the reaction to be conducted at a lower temperature as compared with prior or conventional procedures. By at least partially alkoxylating the substrate in the ketone solvent, the potential for crystallization of the partially alkoxylated substrate is disrupted and the partially alkoxylated substrate has a lower melting point than the original substrate thereby permitting it to be more readily further alkoxylated at the reaction temperature. Suitable ketone solvents include, but are not necessarily limited to, methyl isobutyl ketone (MIBK), diethyl ketone (DEK), methyl ethyl ketone, acetone, and other ketones with a low enough boiling point or high enough vapor pressures to allow ready removal with stripping and mixtures thereof. In one non-limiting embodiment, the ketone solvent may be at least partially removed at one or more intermediate points during the alkoxylation reaction, whether or not added ketone solvent is employed. As compared with MIBK, these other ketones have lower boiling points and may be stripped out at lower temperatures in shorter times, and thus most likely, yield products with even lower colors than is possible with MIBK. Thus, in one non-restrictive version, there is an absence of MIBK. In one non-limiting embodiment, acetone is a particularly suitable solvent.

In one non-limiting embodiment the ketone solvent is the only solvent used; there is an absence of non-ketone solvents. Alternatively, other solvents may be used in addition to or alternatively to the ketone solvents mentioned herein. In one non-limiting embodiment acetone is a suitable solvent. However, the same basic ideas and approaches are applicable to similar high melting materials and other solvents. Alternatively, the solvent consists essentially of one or more ketones. It is desirable in most embodiments herein that the ketone solvent should be removed by the end of the process. Removal of the solvent may be accomplished by a variety of processes, including, but are not necessarily limited to, stripping, heating, sparging with nitrogen, application of vacuum, solvent extraction, washing and combinations thereof.

The alkoxylation reaction of the method herein may be conducted over a wide pressure range, in one non-limiting embodiment, from vacuum independently to about 100 psig (0.7 MPa), and in an alternate non-restrictive version from a lower threshold of about 5 (about 0.03 MPa) independently to an upper threshold of about 60 psig (about 0.4 MPa).

In one non-limiting embodiment, the method may be practiced by the following procedure.

1) Crude BPA containing a ketone solvent remaining from the manufacture of the crude BPA is added to the reactor.
2) A catalyst is added to the reactor.
3) If a caustic compound is used as a catalyst, the mixture is dehydrated.
4) The mixture is alkoxylated with a desired amount of EO and/or PO at suitable reaction conditions.
5) Optionally, at least part of the ketone solvent is removed from the reaction mixture at one or more times during the alkoxylation reaction.
6) If a caustic compound is used as a catalyst, the mixture is neutralized (if it is necessary).
7) The product mixture is stripped (if it is necessary) under a vacuum to remove the ketone solvent. If a low-boiling tertiary amine catalyst is used, it is also stripped out at this step. However, it will be appreciated that in some alternate embodiments, it may be acceptable to leave the solvent and/or the tertiary amine in the product, depending on the eventual end use of the alkoxylated substrate, for instance if the alkoxylated substrate is to be crosslinked with an epoxy resin.

The above steps 1) through 7) may be conducted in the absence of added ketone solvent.

The inventive method will be further disclosed and described with respect to specific embodiments which are only intended to provide illustrative examples, but not to limit the invention in any way.

EXAMPLE 1

Example 1 was started by charging 25 pounds (11.3 kg) of BPA, 8.33 pounds (3.8 kg) of MIBK and 0.54 pounds (0.24 kg) of 45% KOH into a reactor. After dehydrating to a % water content of 0.06, ethoxylation was started and continued until about 20 moles of EO were added per mole of BPA, with about a quart sample taken at intervals of increments of 2 moles of EO per mole of BPA. The reaction was completed and the batch discharged.

A quart sample at the 12-mole EO stage from Example 1 was used to try out stripping the MIBK. The sample was not neutralized and it turned dark when the temperature passed about 130° C. The highest temperature used was 150° C.

EXAMPLE 2

Example 2 was started for making a 6-mole adduct by charging 25 pounds (11.3 kg) of BPA, 10.72 pounds (4.9 kg)

of MIBK and 0.33 pounds (0.15 kg) of 45% KOH into a reactor. The mixture was dehydrated at 130° C. with vacuum and a nitrogen sparge to a % water of 0.024 and then ethoxylated at 130° C. This sample was analyzed by GC and found to have less than 50 ppm of residual MIBK.

Some of the 6-mole adduct from the Example 2 was neutralized to a pH of 6.4 and the sample stripped by heating under 28" of Hg (95 kPa) vacuum. MIBK was observed to start coming out at about 78° C. and approximately 89% of the MIBK came out when the temperature reached 122° C. Little additional MIBK was collected as the batch temperature was raised to 135° C. This is an example of at least partially removing the MIBK solvent at one point during the reaction.

EXAMPLE 3

Example 3 was started by charging 25 pounds (11.3 kg) of BPA, 10.71 pounds (4.9 kg) of MIBK and 0.24 pounds (0.11) of 45% KOH into a 15-gallon reactor (57 liter) for making the two samples subsequently ethoxylated with 2.2 and 4 moles of EO, respectively.

EXAMPLE 4

Example 4 was conducted with 30% MIBK and aqueous KOH for making some sample of the 6-mole EO adduct of BPA for obtaining process data such as batch time and analytical results on the product such as OH#, viscosity, color, etc. The process time from charging the raw materials, through drying, adding ethylene oxide, allowing the charged oxide to react in, taking a sample at about 95% of the full amount of calculated amount of oxide charge to analyzing the sample for OH # was about 14-15 hours. Making two ethylene oxide adjustments took about 7 hours and doing the neutralizing and stripping took about 6 hours.

EXAMPLE 5

Example 5 was conducted with 30% of MIBK from an alternate source and with aqueous KOH to generate a sample of a 2.2 mole adduct of BPA for analysis and to further study the MIBK solvent process including the stripping of MIBK solvent. This is another instance of removing at least part of the ketone solvent at an intermediate point in the reaction. The process time from the time of charging raw materials to the completion of ethoxylation was about 12 hours and about 6 more hours were spent on neutralization, stripping and discharging the product, resulting in a total batch time of about 18 hours.

EXAMPLE 6

Example 6 was conducted similarly to Example 5 with the target end product being about 2.2 mole adduct of BPA except that the solvent used was diethyl ketone (DEK) instead of methyl isobutyl ketone (MIBK). MIBK boils at 118° C. but DEK boils at 101° C., 17° C. degrees lower. With a much lower boiling point, DEK should be able to be stripped out more readily at a lower temperature, the batch time should be shorter and the product color should be lighter. The process time for Example 6 from the time of charging raw materials to the completion of ethoxylation was about 10 hours and about 4 more hours were spent on neutralization, stripping and discharging the product, resulting in a total batch time of about 14 hours. Therefore, based on the results from Examples 5 and 6, the use of DEK allows shorter batch time.

EXAMPLE 7

Example 7 was conducted similarly to Example 5 with the target end product being the 2.2 mole adduct of BPA except that triethylamine, TEA, instead of KOH was used for catalysis. An objective was to determine if a tertiary amine could be used for catalyzing ethoxylation of BPA. Catalyzing with a tertiary amine does not generate water and there is no need to heat to >100° C. to dry the substrate (unless the substrate is already wet), allowing ketones with lower boiling point to be used. The results of Example 7 showed that TEA could be used. The time for adding EO was about 4.5 hours as compared with about 3 hours for a reaction catalyzed with KOH. The process time from the time of charging of raw materials to the completion of ethoxylation was about 7 hours. Therefore, even though the ethoxylation time was longer, the batch time was actually shorter because no dehydration and no neutralization before stripping were needed. Additional advantages for using TEA are 1) that the catalyst TEA can be removed with stripping, 2) that the TEA is reused when the MIBK is reused for a subsequent batch, and 3) that there might be sufficient TEA in the recycled MIBK that no additional TEA needs to be added for the subsequent batch, thus saving catalyst and time to catalyze the reaction. Examples 6 and 7 are further non-limiting instances where at least a portion of the ketone solvent was removed at an intermediate point in the reaction.

EXAMPLES 8, 9, 10, 11 AND 12

Five experiments, Examples 8, 9, 10, 11, and 12, were conducted with samples obtained from reactions in Examples 2, 3 and 4 to determine the conditions needed for stripping out MIBK and how low a level could be achieved. These are further examples of removing at least a portion of the ketone solvent during the alkoxylation reaction. The samples were stripped at temperatures from 70 to 145° C. and with a vacuum of −12 psig to 28" of Hg (82 to 95 kPa). It had been shown that an un-neutralized sample would turn dark during stripping at elevated temperatures. Therefore, all the samples were neutralized with glacial acetic acid before heating up for stripping. MIBK was observed to start distilling over at about 70° C. and about 12-14" of vacuum (40.6 to 47.4 kPa). To prevent "burping", the temperature was raised and vacuum increased stepwise. No more MIBK was observed being distilled over or collected after about 0.5 hour at 130° C. with about 28" of Hg (95 kPa) of vacuum. Temperatures higher than 130° C. did not seem to be necessary and would cause the product to be darker. Samples from Examples 8 and 9 were analyzed for residual MIBK. The samples were analyzed by GC and were found to contain less than 50 ppm of residual MIBK.

It should be noted that all of the approximately 2.2 mole EO adducts were solid at ambient temperature and became pourable at about 100° C., and that 6-mole samples are pourable at ambient temperature.

EXAMPLE 13

Example 13 was conducted to make a 6-mole EO adduct of BPA. The batch was made with the use of tributylamine, TBA, rather than 45% KOH for catalysis. As compared with triethylamine, which has a boiling point of 90° C. and was used to make a batch of BPA-2EO in Example 7, TBA has a boiling point of 216-217° C. Thus, it was desired to find out to what extent TBA would be removed during the stripping of the MIBK solvent. The batch time for Example 13 was at least 2 hours shorter than that for the batch made with KOH for catalysis due to time saving from not having to dehydrate before ethoxylation and not having to neutralize before stripping MIBK.

Since there is no need for dehydration with the use of a tertiary amine for catalysis, there is no loss of solvent as has occurred during dehydration with a nitrogen sparge and/or with the application of vacuum. With no loss of solvent, the mass balances are more accurate and there is less need for having to take a sample at the end of dehydration for determining the amount of solvent lost by running OH# analysis, etc. and there is less need for having to make cuts by charging less than the full amount of oxides in order to avoid overcharging, thus allowing more saving on batch time.

EXAMPLE 14

Example 14 was conducted in order to make ethoxylates with the number of moles of oxide closer to the targeted values and to produce enough material at the 2-mole stage for using as starting material for making higher adducts. 25 lbs (11.4 kg) of BPA, 10.8 lbs (4.9 kg) of MIBK and 0.37 lbs (0.17 kg) of TBA were charged to a reactor. The mixture was heated to 120° C., the reactor was deareated and EO was charged at 120-130° C. 6.94 lbs (3.15 kg) and 7.8 lbs (3.5 kg) of products were drained out at the 2.2-mole and 4-mole stages, respectively. More oxide was then added to make the 6-mole adduct.

From the time when BPA was charged to when oxide had reacted down for the 6-mole adduct, the batch time was 12.8 hours, including the "extra" time allowed for charged ethylene oxide to react in and for taking the two cuts. After the charged oxide for the 6-mole adduct had reacted in, the batch was cooled to about 116° C. to avoid flash boiling out of MIBK and then reheated stepwise to about 128° C. under vacuum for stripping out MIBK. The time for stripping was 3 hours. The batch was then cooled and 36.6 lbs (16.6 kg) of final stripped 6-mole adduct were discharged. The total batch time for Example 14 was about 17-18 hours, which included the extra time allowed for making the two cuts. The OH# for the 6-mole adduct was 235.2 and the acid # was 0.48. The OH# spec for the 6-mole adduct was 220-240.

The 2.2-mole adduct from Example 14 set up hard and could not be remelted. It may be understood that an additional potential advantage of the ketone process described herein is that the 2.2-mole adduct, and also other adducts that solidify at ambient temperature, may be provided in solution form for those customers who may wish to receive the materials in solution form for easy handling. That is, the ketone solvent need not be removed.

1762 grams of the 4-mole adduct from Example 14 was charged into a glass vessel and stripped under vacuum. 1398.5 grams of material were discharged after stripping. The stripped material was analyzed to have an OH# of 259.6 and an Acid # of 0.17.

EXAMPLE 15

Example 15 was conducted to make the 2.2-mole adduct in a reactor and to have the adduct stripped in the same reactor. The total batch time was about 17 hours and the stripped sample had an OH# of 335 (specification: 330-350).

EXAMPLE 16

When 5 gallons (15 liters) of a "wide-spec" BPA material arrived, some of it was used to conduct Example 16 for making a 6-mole adduct. This "wide-spec" BPA material had some (a few) brownish specks and clumps in the otherwise white lumpy and powdery material. The batch time was about 18 hours and the final product had an OH# of 226. The color of the product was amber as compared with the slight yellow color of products made from good "on-spec" BPA.

EXAMPLE 17

An additional Example was conducted to make the 6-mole adduct with good "on-spec" BPA. The batch time was 17 hours. The final product was analyzed to have an OH# of 225 and a light yellow color.

EXAMPLE 18

It was desired to collect data on the time that would take to melt bisphenol A in MIBK inside a reactor without agitation and to confirm material balances especially for MIBK during distillation. Example 18 was prepared by charging MIBK and solid Bisphenol A into the reactor. The reactor was then heated without agitation and it was found that it took about 3 hours to have BPA melted and dissolved in MIBK. The batch was then catalyzed with TBA, ethoxylated and stripped. The data on mass balances confirmed what was reported above. The batch time was about 19 hours and the OH# was 221. The data for Examples 14-18 are summarized in Table I:

TABLE I

Summary of Data from Examples 14-18

| Ex. | Targeted # of moles | Empirical OH # | Specifications | Batch time, approx. hours |
|---|---|---|---|---|
| 14 | 6 | 235.2 | 220-240 | 18 |
| 15 | 2.2 | 335 | 330-350 | 17 |
| 16 | 6 | 226 | 220-240 | 18 |
| 17 | 6 | 225 | 220-240 | 17 |
| 18 | 6 | 221 | — | 19 |

EXAMPLE 19

Procedure for Making Bisphenol A with 6 Moles EO in MIBK Solvent and with the Use of Amine Catalyst (Weights are for a 15-Gallon Batch)

1. With the reactor charge hatch or charge port open and with a vacuum on reactor to pull away dust, charge reactor with:

| Bisphenol A | MW = 228.31 | 38.37 wt % | 25.00 lbs (11.4 kg) |
|---|---|---|---|

2. Close reactor hatch or charge port, pull a 20 inches vacuum (68 kPa), and add:

| MIBK (Methyl Isobutyl Ketone) | 16.38 wt % | 10.67 lbs (4.83 kg) |
|---|---|---|
| Tributyl Amine | 0.74% | 0.48 lbs (217g) |

3. Pull vacuum to 20-24 inches (68-81 kPa), release the vacuum and pressureize with nitrogen to 20 psig (138 kPa). Release the nitrogen pressure to about 5 psig (about 35 kPa) and repressurize the reactor with nitrogen to about 30-40 psig (about 210-280 kPa). Release the reactor pressure to 5 psig. Turn on the agitator and heat to 125° C.

4. Increase agitator speed after reaching 125° C. At 125-130° C. begin adding EO. Continue to add:

| EO (Ethylene Oxide) | 44.51% | 29.5 lbs (13.4 kg) |
|---|---|---| while controlling the temperature between 125-135° C.
5. After the EO addition is finished, allow all charged EO to react in at 130-135° C. for one hour.
6. Neutralize an 8-ounce (0.2 liter) sample, strip out MIBK and determine the hydroxyl number.
Specification: Hydroxyl Number about 230 (225 to 240)
7. If OH# is within specification, proceed to distill out the MIBK using nitrogen and maximum vacuum at 118-130° C.
8. Weigh the MIBK coming out to determine when the MIBK has finished coming over.
9. When the MIBK has distilled out, cool to 80° C. and discharged, the Yield should be 82.8%, or about 54.5 lbs (24.7 kg).

From these Examples it may be seen that alkoxylations of high melting point substrates having at least one active hydrogen atom (e.g. BPA) may be advantageously conducted using ketone solvents using either a caustic compound as catalyst or a tertiary amine catalyst.

Thus the methods herein are successful for reacting alkylene oxides with active hydrogen-containing substrates, which have high melting points, at a reduced temperature, without melting the substrates, which allows the use of more readily available and less costly reactor systems heated by steam in contrast to systems heated by hot-oils and/or which require heat tracing of the pipes and valves. They are further able to produce alkylene oxide adducts having reduced color and less by-products.

In the foregoing specification, the invention has been described with reference to specific embodiments thereof, and has been demonstrated as effective in providing an alternate method of ethoxylating BPA, as a non-limiting example. However, it will be evident that various modifications and changes can be made thereto without departing from the broader scope of the invention as set forth in the appended claims. Accordingly, the specification is to be regarded in an illustrative rather than in a restrictive sense. For example, specific substrates, whether in crude or pure or substantially pure form, alkylene oxides, ketone solvents, catalysts, and reaction conditions falling within the claimed parameters, but not specifically identified or tried in a particular reaction to produce a less colored adduct product with less degradation by-products, are within the scope of this invention. Similarly, it is expected that there may be other advantages to using ketone solvents other than reducing the reaction temperature and producing a product with reduced color that may yet be determined.

The words "comprising" and "comprises" as used throughout the claims is interpreted "including but not limited to". The present invention may suitably comprise, consist or consist essentially of the elements disclosed and may be practiced in the absence of an element not disclosed.

In another non-limiting embodiment there may be provided a method for producing a fully alkoxylated bisphenol A that consists essentially of or consists of mixing a compound selected from the group consisting of an alkylene oxide and an arylene oxide, with crude bisphenol A containing a ketone solvent remaining from the manufacture of the crude bisphenol A, with a catalyst to give a reaction mixture, where the catalyst is selected from the group consisting of a tertiary amine catalyst, and a caustic compound selected from the group consisting of potassium hydroxide and sodium hydroxide; where the method further consists essentially of or consists of reacting the compound with the bisphenol A in the reaction mixture at a reaction temperature in the range of about 30 to 140° C. to give an at least partially alkoxylated bisphenol A sufficiently alkoxylated to lower its melting point below the reaction temperature; and continuing to alkoxylate the at least partially alkoxylated bisphenol A to give the fully alkoxylated bisphenol A; where the method is conducted in the absence of added ketone solvent.

What is claimed is:

1. A method for producing a fully alkoxylated bisphenol A comprising:
    mixing:
        a compound selected from the group consisting of an alkylene oxide and an arylene oxide, with
        crude bisphenol A containing a ketone solvent remaining from the manufacture of the crude bisphenol A, with
        a catalyst to give a reaction mixture, where the catalyst is selected from the group consisting of:
            a tertiary amine catalyst, and
            a caustic compound selected from the group consisting of potassium hydroxide and sodium hydroxide,
    reacting the compound with the bisphenol A in the reaction mixture at a reaction temperature in the range of about 30 to 140° C. to give an at least partially alkoxylated bisphenol A sufficiently alkoxylated to lower its melting point below the reaction temperature; and
    continuing to alkoxylate the at least partially alkoxylated bisphenol A to give the fully alkoxylated bisphenol A;
    where the method is conducted in the absence of added ketone solvent.

2. The method of claim 1 where the compound selected from the group consisting of alkylene oxide and arylene oxide is selected from the group consisting of ethylene oxide, propylene oxide, butylene oxide, styrene oxide and mixtures thereof.

3. The method of claim 1 where the ketone solvent is selected from the group consisting of methyl isobutyl ketone, diethyl ketone, methyl ethyl ketone, acetone, and mixtures thereof.

4. The method of claim 1 where the reaction is conducted at a pressure in the range from about 5 psig (about 0.03 MPa) to about 100 psig (0.7 MPa).

5. The method of claim 1 where the catalyst is a tertiary amine catalyst and the method is practiced in the absence of a dehydration step.

6. The method of claim 5 where the method is practiced in the absence of a neutralization step.

7. The method of claim 5 where the catalyst is selected from the group consisting of triethylamine, tributylamine, methyl alkyl amines, dimethyl alkyl amines, and mixtures thereof.

8. The method of claim 1 where the catalyst is a caustic compound and the method further comprises:
    heating the reaction mixture to dehydrate it; and
    neutralizing the reaction mixture.

9. A method for producing a fully alkoxylated bisphenol A comprising:
    mixing crude bisphenol A containing a ketone solvent remaining from the manufacture of the crude bisphenol A, with a caustic compound catalyst to give a mixture, where the catalyst is selected from the group consisting of potassium hydroxide and sodium hydroxide;
    heating the mixture to dehydrate it;

adding a compound selected from the group consisting of alkylene oxide and arylene oxide, to the mixture to give a reaction mixture;

reacting the compound with the bisphenol A in the reaction mixture at a reaction temperature in the range of about 30 to 140° C. to give an at least partially alkoxylated bisphenol A sufficiently alkoxylated to lower its melting point below the reaction temperature; and continuing to alkoxylate the at least partially alkoxylated bisphenol A to give the fully alkoxylated bisphenol A;

where the method is conducted in the absence of added ketone solvent.

10. The method of claim 9 where the compound selected from the group consisting of alkylene oxide and arylene oxide is selected from the group consisting of ethylene oxide, propylene oxide, butylene oxide, and styrene oxide and mixtures thereof.

11. The method of claim 9 where the ketone solvent is selected from the group consisting of methyl isobutyl ketone, diethyl ketone, methyl ethyl ketone, acetone, and mixtures thereof.

12. The method of claim 9 where the reaction is conducted at a pressure in the range from about 5 psig (about 0.03 MPa) to about 100 psig (0.7 MPa).

13. A method for producing a fully alkoxylated bisphenol A comprising:

mixing crude bisphenol A containing a ketone solvent remaining from the manufacture of the crude bisphenol A, with a tertiary amine catalyst to give a mixture;

adding a compound selected from the group consisting of alkylene oxide and arylene oxide, to the mixture to give a reaction mixture;

reacting the compound with the bisphenol A in the reaction mixture at a temperature in the range of about 30 to 140° C. to give an at least partially alkoxylated bisphenol A sufficiently alkoxylated to lower its melting point below the reaction temperature; and continuing to alkoxylate the at least partially alkoxylated bisphenol A to give the fully alkoxylated bisphenol A;

where the method is conducted in the absence of added ketone solvent.

14. The method of claim 13 where the compound selected from the group consisting of alkylene oxide and arylene oxide is selected from the group consisting of ethylene oxide, propylene oxide, butylene oxide, and styrene oxide and mixtures thereof.

15. The method of claim 13 where the ketone solvent is selected from the group consisting of methyl isobutyl ketone, diethyl ketone, methyl ethyl ketone, acetone, and mixtures thereof.

16. The method of claim 13 where the reaction is conducted at a pressure in the range from about 5 psig (about 0.03 MPa) to about 100 psig (0.7 MPa).

17. The method of claim 13 where the method is practiced in the absence of a dehydration step.

18. The method of claim 13 where the method is practiced in the absence of a neutralization step.

19. The method of claim 13 where the catalyst is selected from the group consisting of triethylamine, tributylamine, methyl alkyl amines, dimethyl alkyl amines, and mixtures thereof.

\* \* \* \* \*